(12) United States Patent
Jacops et al.

(10) Patent No.: US 8,586,121 B2
(45) Date of Patent: Nov. 19, 2013

(54) FRUIT SNACK

(75) Inventors: Luc Leo Ivonne Jacops, Boulwel (BE); Natasja Veronica Hermina Lemmens-Smink, Veghel (NL); Vincent Yves Gerard Passard, Sandridge (GB)

(73) Assignee: Mars, Inc., McLean, VA (US)

( * ) Notice: Subject to any disclaimer, the term of this patent is extended or adjusted under 35 U.S.C. 154(b) by 1384 days.

(21) Appl. No.: 11/773,028

(22) Filed: Jul. 3, 2007

(65) Prior Publication Data

US 2008/0014303 A1 Jan. 17, 2008

(30) Foreign Application Priority Data

Jul. 22, 2005 (GB) .................................. 0515173.3
Aug. 24, 2005 (GB) .................................. 0517354.7
Jul. 21, 2006 (WO) ................ PCT/GB2006/002725

(51) Int. Cl.
*A23L 1/05* (2006.01)
(52) U.S. Cl.
USPC .......................................... 426/577; 426/410
(58) Field of Classification Search
USPC ......... 426/50, 90, 92, 94, 100, 101, 102, 577, 426/410
See application file for complete search history.

(56) References Cited

U.S. PATENT DOCUMENTS

| | | | |
|---|---|---|---|
| 4,562,080 A | 12/1985 | Tenn | |
| 5,639,494 A * | 6/1997 | Grassin et al. | 426/50 |
| 5,840,353 A * | 11/1998 | Wilding et al. | 426/15 |
| 6,309,679 B1 | 10/2001 | Spencer | |
| 2002/0015758 A1 | 2/2002 | Kreiberg et al. | |

FOREIGN PATENT DOCUMENTS

| | | |
|---|---|---|
| EP | 0599677 A1 | 6/1994 |
| EP | 0624062 A1 | 11/1994 |
| EP | 1009246 A1 | 6/2000 |
| EP | 1022959 A1 | 8/2000 |
| EP | 1431313 | 6/2004 |
| EP | 1554939 A1 | 7/2005 |
| EP | 1567019 A1 | 8/2005 |
| JP | 61-40737 A | 2/1986 |
| JP | 06-098712 A | 4/1994 |
| JP | 7000154 A | 1/1995 |
| JP | 07-155130 A | 6/1995 |
| JP | 2001-292711 A | 10/2001 |
| JP | 2004-89181 A | 3/2004 |
| JP | 2004-180542 A | 7/2004 |
| WO | 9412055 A1 | 6/1994 |

(Continued)

OTHER PUBLICATIONS

Zeuthen, Peter; Bøgh-Sørensen, Leif Food Preservation Techniques. (pp. 109-120). Woodhead Publishing. 2003, no month given. Online version available at: http://knovel.com/web/portal/browse/display?_EXT_KNOVEL_DISPLAY_bookid=1248 &VerticalID=0.*

(Continued)

*Primary Examiner* — Rena Dye
*Assistant Examiner* — Chaim Smith
(74) *Attorney, Agent, or Firm* — Fulbright & Jaworski LLP

(57) ABSTRACT

The present invention is directed to a packaged, shelf-stable, gelled natural fruit pulp, in which the natural pectins of the fruit pulp have been substantially demethoxylated by the action of a pectinmethylesterase enzyme under ultra-high pressure (UHP) conditions. Also provided is a method of preparation of the packaged, ambient-stable, natural fruit product.

21 Claims, 1 Drawing Sheet

(56) References Cited

FOREIGN PATENT DOCUMENTS

| WO | WO-9412055 | | 6/1994 | |
| --- | --- | --- | --- | --- |
| WO | 9611588 A1 | | 4/1996 | |
| WO | WO 97/10726 | * | 3/1997 | ............ A23L 1/0522 |
| WO | WO-9738591 | | 10/1997 | |
| WO | 9911148 A1 | | 3/1999 | |
| WO | 9918813 A1 | | 4/1999 | |
| WO | WO-0158286 | | 8/2001 | |
| WO | WO-0207530 | | 1/2002 | |
| WO | 2004049824 A1 | | 6/2004 | |

OTHER PUBLICATIONS

Doona, Christopher J.; Feeherry, Florence E. High Pressure Processing of Foods. (pp. 3-4). John Wiley & Sons. 2007, no month given. Online version available at: http://knovel.com/web/portal/browse/display?_EXT_KNOVEL_DISPLAY_bookid=2853&VerticalID=0.*

Machine Translation of Schnitzler et al. WO 0207530, Jan. 2002.*

US PTO translation of Schnitzler WO 02/07530 Jan. 2002.*

International Preliminary Report on Patentability issued Jan. 22 2008, (Published Jan. 22, 2008), during the prosecution of International Application No. PCT/GB2006/002725.

International Search Report issued Sep. 27, 2006, (Pub Jan. 25, 2007), during the prosecution of International Application No. PCT/GB2006/002725.

Written Opinion issued Sep. 27, 2006, (Pub Jan. 22, 2008), during the prosecution of International Application No. PCT/GB2006/002725.

Susumo at al, "Increase in Viscosity and Gel Formation of Fruit Juice by Purified Pectinesterase," Faculty of Science, Osaka city University, Osaka, received Jun. 5, 1965, Agr. Biol. Chem., vol. 29, 10:936-942.

* cited by examiner though to make the final product palatable sweeteners and flavorings may be added. Preferably, the only added ingredient

FRUIT SNACK

CROSS-REFERENCE TO RELATED APPLICATIONS

This application is a national stage application of PCT/GB2006/002725 filed Jul. 21, 2006 claiming priority to GB 0515173.3 filed Jul. 22, 2005 and GB 0517345.7 filed Aug. 24, 2006.

TECHNICAL FIELD

The present invention relates to packaged, shelf-stable, natural fruit snack products, and to methods of preparation thereof.

BACKGROUND OF THE INVENTION

Increased health awareness has led to increased consumption of fresh fruit as a snack food. However, fresh fruits are seasonal, and undergo fairly rapid spoilage. Furthermore, certain fresh fruits such as mango are not easy to consume as a snack food, especially by children.

WO 02/07530 describes a high-fiber vegetable and fruit snack food in the form of a packaged, stabilized bar. The products are made by partially draining liquid from a fruit pulp to produce a high-fiber pulp, and adding a hydrocolloid such as a modified pectin to solidfy the pulp. The resulting product is formed into a bar, packaged, and stablized for example by application of ultra-high pressure (UHP). The products have a solid, chewy consistency due to the high fiber content and the presence of added hydrocolloid. This product is therefore less palatable than fresh fruit or jelly.

WO 94/12055 discloses a method for preparing a fruit or vegetable gel comprising the steps of: the addition of pectinesterase to the fruit or vegetable or to the pulp thereof to demethoxylate a pectin; optionally the addition of calcium chloride; allowing the fruit derived demethoxylated pectin to form a gel; and formulating the thus-treated fruit or vegetable to obtain the desired food. The product is not stable or packaged, and is intended as an intermediate for addition to dairy, bakery or confectionery products.

Susumo Oi and Yukio Satomura in *Agr. Biol. Chem.* Vol. 29(10), pages 936-942 (1965) describe research into the treatment of fruit juices with a purified pectinmethylesterase (PME) enzyme, optionally with the addition of a calcium salt. The treatment increased the viscosity of the fruit juices. Extended treatment for 200 minutes or more caused some of the juices to form gels. The reference does not discuss stabilization of the gels, nor does it suggest the use of PME for the production of gelled fruit pulps.

WO97/38591 describes improved cold break tomato puree produced by the steps of: (a) applying UHP to inactivate polygalacturonase (PG) but not PME enzymes, (b) incubating the tomato puree with the PME to achieve a thickened consistency, followed by (c) inactivating the PME with heat. There is no disclosure of shelf-stable, packaged, gelled products. Moreover, incubation of tomato puree with PME results in a thickened, but not gelled, product.

EP-A-1431313 describes gelled compositions having a natural fruit texture prepared by treating a sweetened, flavored aqueous solution (not a fruit pulp) with a very low methoxy pectin, calcium, and additional hydrocolloids such as edible gums. The resulting jellies are said to have an in-homogeneous texture similar to that of natural fruit flesh. The jellies may be packaged in a pouch container for direct consumption, in which case they may be thermally stabilized, for example by heating at 90° C. for 20 minutes.

A need remains for a packaged, shelf-stable fresh fruit product that is dimensionally stable for convenient consumption, and that retains the color, flavor, aroma and nutritional qualities of fresh fruit.

BRIEF SUMMARY OF THE INVENTION

The present inventors have devised methods of making such products. The methods further have the advantages of minimal processing and minimal use of non-fruit ingredients.

In a first aspect the present invention provides a packaged, shelf-stable, gelled natural fruit pulp, wherein the natural pectins of said fruit pulp have been substantially demethoxylated by the action of a pectinmethylesterase enzyme under UHP conditions.

In a second aspect, the present invention provides a method of preparation of a packaged, ambient-stable, natural fruit product comprising the following steps:
 (a) comminuting a fresh fruit to provide a first fresh fruit pulp;
 (b) adding a PME enzyme to the first fresh fruit pulp;
 (c) packaging the first fresh fruit pulp and PME in a sealed, substantially oxygen-impermeable container;
 (d) incubating the fresh fruit pulp and PME under UHP to demethoxylate natural fruit pectins in said pulp and thereby convert the pulp to a dimensionally stable gel bar and render the product shelf-stable.

The present invention modifies the pectins that are naturally present in the fruit (i.e. endogenous pectins) to gel the fruit pulp. The pectins are demethoxylated by the action of added PME under controlled incubation conditions to produce demethoxylated pectins that form a gel with the water naturally present in the fruit pulp, and thereby bind the fruit pulp into a dimensionally stable gel matrix. Gel formation can be recognized, for example, by mechanical properties of the product. In particular, the product is semi-solid and dimensionally stable, typically with a texture intermediate that of natural fruit flesh and jelly. Gel formation can also be recognized by thermal analysis, as the pectin gel will have a melting point endotherm that is detectable by differential scanning calorimetry.

The present inventors have found that, by incubation under UHP conditions, the fruit pulp can be bound into a dimensionally stable snack bar-type product without the addition of any other hydrocolloids, and without the addition of sugar, and frequently without even the addition of divalent ions such as calcium to promote gelling. This enables the production of dimensionally stable fruit snack products having full moisture and a highly natural flavor at minimal cost. The present inventors have further found the fruit bar products can be rendered shelf-stable under mild temperature conditions by appropriate choice of high pressure treatment and appropriate choice of packaging. The mild stabilization treatment also gives the fruit bar product with a fresh, natural appearance, flavor, aroma and moisture content. In contrast to above-described existing methods for fruit gel production, the methods of the present invention can start from full moisture fresh fruit pulp without addition of any hydrocolloids or other additives other than PME, and without processing at elevated temperatures.

In principle the present invention is applicable to a wide variety of fruits including mango, strawberry, kiwi fruit, papaya, pineapple, apricot, peach, nectarine, cherries, blueberries, raspberries, apple, pear, chestnut, tropical fruit, banana, prunes, blackberry, cranberry, passion fruit, grapefruit, lemon, mandarin, orange, melon, grapes, and mixtures thereof. In certain embodiments, the fruit pulp could include vegetable pulps such as carrot or pepper. It has been found that fruits in which the principal pigment is a carotenoid exhibited greater color stability following high pressure stabilization than fruits in which the principal pigment is a chlorophyll (e.g. kiwi fruit) or an anthocyanin (e.g. strawberries and raspberries). Furthermore, the carotenoid-pigmented fruits mango, papaya, apricot, nectarine and peach have also been found to form products with excellent mechanical and organoleptic properties.

In certain embodiments, the gel-forming fruit pulp may be a mixture of different fruits, for example mango and another fruit, preferably apple and mango. As already noted, mango, papaya, apricot, nectarine and/or peach are preferred as a major component of the fruit pulp (at least 25% by weight, more preferably at least 50% by weight), especially when the process comprises a high pressure stabilization step. In certain embodiments, the products according to the present invention may comprise a region of a first fruit pulp composition and a second region of a second fruit pulp composition different from the first fruit pulp composition. For example, the product may comprise an outer shell of the first fruit pulp composition and an inner core of the second fruit pulp composition. In these embodiments, only the outer shell needs to be a gelled pulp. The inner core may not be gelled, or it may be gelled with a lower gel strength than the outer core. This can be achieved by forming the core from a fruit pulp that is substantially free from added PME, and/or that contains a PME inhibitor, and/or from a fruit pulp having low endogenous pectin content. These configurations permit a wider range of colors, textures and/or fruit types to be used for the core. For example, in certain embodiments, the shell comprises a major fraction of mango, papaya, peach, nectarine or apricot and the core comprises a major fraction of pineapple pulp. In certain embodiments, the contrast between the regions can be enhanced by use of fruits having different natural coloration, and/or by addition of food-acceptable colorants to one or both regions. The colorant may be in an oil-based dispersion to reduce migration between the regions.

The term "fruit" refers generally to the edible portions of fruit, e.g. fruit flesh and edible fruit skins. The products according to the invention generally do not contain fruit seeds or stones having maximum dimension greater than about 2 mm, nor do they generally contain thick fruit peels such as mango peel or apple peel. Preferably, the fruit pulp consists essentially of comminuted fruit flesh. The term "natural fruit pulp" herein refers to a pulp obtained by comminuting a natural, fresh fruit. The pulp may comprise, or consist essentially of, a pulp that has been concentrated by evaporation or other means, or it may consist essentially of full moisture fruit pulp. However, the pulp preferably has not been treated at a temperature above about 70° C., and more preferably it has not been treated at a temperature above about 50° C. It will be appreciated that the fruit may have been frozen for storage and/or transport either before or after comminution to produce the pulp.

The fruit (e.g. fruit flesh) is comminuted to a fruit pulp. The fruit pulp may be a substantially smooth puree or it may be a more loosely chopped pulp e.g. containing pieces larger than about 1 mm maximum dimension, for example pieces having maximum dimensions of from about 1 mm to about 5 mm. Or it may be a mixture of smooth puree and larger pieces. The inclusion of some fruit pieces in the pulp provides a non-uniform texture final product that may be preferred by consumers. Preferably, the fruit pulp is a whole fruit pulp, that is to say none of the components of the fruit flesh is removed before subsequent processing steps. In particular, substantially the whole moisture content of the fruit flesh is preferably retained in the pulp. Typically, the fruit pulp has a water content of at least 70 wt. %, more preferably at least 80 wt. %, and in some embodiments at least 90 wt. % water.

The pulp may optionally comprise added dietary fiber, but generally it does not. Preferably, the pulp contains less than about 15 wt. % of insoluble fiber, more preferably less than about 10 wt. % of insoluble fiber, still more preferably less than 8 wt. % fiber, more preferably less than about 5 wt. % of insoluble fiber. Preferred ranges for the insoluble fiber content are from about 0.1 wt. % to about 3 wt. %, for example from about 0.5 wt. % to about 2 wt. %. Insoluble fiber content is determined by AOAC Method 991.43.

Preferably, the step of comminuting the fruit to form the pulp is performed at temperatures below 50° C., more preferably below about 40° C., e.g. at ambient temperature. This allows the whole flavor, aroma and nutritive quality of the fruit to be retained in the pulp.

It is an advantage of the present invention that the fruit pulp, in addition to being minimally processed, preferably contains minimal additives. This is because the processing method allows a coherent product to be made generally without the addition of binders, hydrocolloids and/or saccharides.

Preferably, the fruit pulp and the final product are substantially free from added hydrocolloids, that is to say hydrocolloids other than those present or derived from the hydrocolloids present in the original fruit pulp. Where present, the added hydrocolloids may for example be selected from the group consisting of added pectin, added demethoxylated pectin, an alginate, or a food acceptable polysaccharide gum. Where present, the total amount of added hydrocolloids is suitably from about 0.05% to about 1% based on the weight of the pulp, more preferably from about 0.1% to about 0.5 wt. %.

The fruit pulp may comprise an added divalent metal ion salt to promote gelling of the demethoxylated pectin. Suitable divalent metal ions are calcium ions, for example in the form of calcium chloride or calcium acetate or calcium lactate or calcium lactate gluconate or calcium ascorbate. Calcium lactate is preferred. The addition of divalent metal ion salt is not necessary in all cases. For example, mango contains sufficient endogenous calcium for satisfactory gelling without addition of divalent metal ion salts. On the other hand, addition of calcium salts is necessary to achieve satisfactory gelling of apple pulp. Where present, the divalent metal ion salt is suitably added in an amount (as $Ca^{2+}$) of from about 0.05 to about 3 wt. %, preferably from about 0.05 wt. % to about 0.4 wt. %.

The pH of the fruit pulp and of the final product is preferably less than about 4.5, more preferably in the range of from about 3 to about 4, most preferably from about 3 to about 3.5. The pH is measured directly on the pulp without dilution, at ambient temperature. This pH range may be inherent of the fruit pulp, or the fruit pulp may optionally contain a food acceptable acid to buffer the pH to the desired range. Suitable food-acceptable acids include citric acid, ascorbic acid, malic acid, tartaric acid, lactic acid, salicylic acid, ferulic acid. Fruit acids occurring in the fresh fruit are especially suitable. Where present, the food-acceptable acid is preferably added in an amount of from about 0.1 wt. % to about 4 wt. %, preferably from about 0.1 wt. % to about 2 wt. %, based on the total weight of the fruit pulp.

In certain embodiments the fruit pulp and the final product may contain an added antioxidant to promote stability. A suitable antioxidants is ascorbic acid, which of course may also function as an acidulant. Preferably, the antioxidant is present in an amount of from about 0.1 wt. % to about 4 wt. %, preferably from about 0.1 wt. % to about 2 wt. %, based on the total weight of the fruit pulp. The ascorbic acid may be derived from natural fruit in the pulp.

Preferably, the fruit pulp and the final product are substantially free from added saccharides. It is the feature of the present process and product that added sugars are not needed in order to achieve satisfactory gelling. Nevertheless, in certain embodiments saccharides may be added for flavoring or other purposes, in which case the saccharides are preferably added in an amount of less than about 50 wt. %, more preferably less than about 30 wt. %, and most preferably less than about 10 wt. % by weight based on the weight of the fruit pulp, for example from about 1 wt. % to about 10 wt. %.

Other sweeteners and flavoring agents may be added to the fruit pulp, but generally it is not necessary to do so because the whole color, flavor and aroma of the fresh fruit are substantially preserved in the products made in accordance with the present invention.

Accordingly, the products according to the present invention preferably consists essentially of the fruit, the added PME, optionally added divalent metal ion salts, the optional acidifier, and the optional antioxidants.

The fruit pulp contains endogenous PME and PG enzymes. The PME de-esterifies the methoxy groups on the pectin chain to leave polygalacturonic acid. The carboxylate groups on the demethoxylated pectin cross-link through divalent metal ions, resulting in gel formation. However, in most fruits including mango when processed in accordance with the present invention, incubation of fruit pulp with the endogenous PME alone is insufficient to produce a coherent, dimensionally stable gel product suitable for consumption as a snack bar. Therefore, it is necessary to add further PME to the fruit pulp.

The PG enzymes depolymerise the pectin chains, and in particular depolymerise the demethoxylated pectin chain in the fruit pulp. It is a further advantage of the present invention that the application of UHP has the effect of at least partially inactivating the endogenous PG in the fruit pulp.

The process according to the present invention includes a step of adding PME to the fruit pulp. The added PME can be obtained from various sources, including plants, bacteria or fungi. PME obtained from a genetically recognized as safe (GRAS) strain of *aspergillus niger* is commercially available, and the production of PME therefore will not be described further. Another preferred source of PME is fruit pulps that are especially rich in PME, for example tomato puree. The use of fruit pulps as a source of PME reduces the number of additives in the pulp and makes possible the preparation of a 100% fruit product.

In certain embodiments, the product consists essentially of fruit pulps. For example, the PME may be derived from added tomato pulp, the acidulant and antioxidant may for example be provided by citric acid and ascorbic acid naturally present in fruit pulps. In these embodiments, the product is at least about 99 wt. % fruit, preferably about 100% fruit.

These products according to the present invention may be 100% organic. The products are preferably substantially or completely free of food additives.

The PME is added to the fruit pulp preferably in an amount of from about 300 to about 9000 PE units per kilogram, more preferably from about 450 to about 3600 PE units per kilogram.

The fruit pulp containing the added PME and optional other ingredients is then packaged. The packaging is suitable for maintaining the fruit product in shelf-stable condition. At least a portion of the packaging may be transparent to allow inspection of the package contents. The packaging is substantially impermeable to microorganisms, and it is also substantially impermeable to gases such as oxygen, in order to maintain the freshness of the product. Preferably, the packaging is substantially oxygen-impermeable. Suitable packaging materials have an oxygen permeability at 23° C./50% relative humidity less than about 2 $cm^3/m^2$/day at 1 atm pressure. Suitable packaging films include oxygen barrier laminates such as C5045 Cryovac, and oxygen scavenging films. It has been found that the combination of oxygen-impermeable packaging with addition of antioxidants such as ascorbic acid results in products that exhibit excellent storage stability when prepared in accordance with the invention.

The packaging may, for example be in the form of a container having rigid walls such as a glass or plastic jar. However, more suitably the package is a flexible pouch. The term "flexible pouch" refers to a closed container formed substantially or completely of a flexible sheet material. The sheet material normally comprises at least one continuous layer of thermoplastic film, or it may be a laminated sheet made up of more than one thermoplastic film layer. The sheet material making up the pouch may further comprise a metal layer, such as an aluminum layer, to render the material oxygen-impermeable and to provide aesthetic effects.

The pulp may be filled into the container in conventional filling or form-fill-seal equipment. The equipment may be adapted to fill the container with regions of two or more different fruit pulps. For example, two different fruit pulps may be filled into the container through concentric filling tubes in similar fashion to so-called "one-shot" confectionery molding methods in order to provide a product having a shell of a first pulp and a core of a second pulp.

As already discussed, the body of the package preferably consists essentially of a pouch of flexible sheet material. The pouch may, for example, be a so-called pillow pouch, typically formed by continuous form-fill-seal equipment, or the pouch may be formed by bonding together front and back faces of flexible sheet materials around their marginal edges. In certain embodiments, the pouch may be a stand-up pouch. That is to say, a pouch formed by bonding together front and back faces of sheet material around three edges, with a gusset sheet inserted and bonded to the respective fourth edges of the front and back sheets to form a base for the pouch. The total thickness of each flexible wall of the pouch is suitably in the range of from 50 micrometers to 1000 micrometers, for example 100 micrometers to 500 micrometers.

The pouch may be provided with a nip and/or a line of weakness and/or a tear strip to allow the pouch to be opened more easily after filling. The volume of the fruit product in the package is suitably from about 20 ml to about 1000 ml, preferably from about 30 ml to about 300 ml, for example from about 50 ml to about 250 ml. This volume is appropriate for containing an individual portion of the fruit product, that is to say a portion suitable for consumption by one human individual at one time. Typically, the fruit product substantially completely fills the package.

The fruit pulp containing the added PME and optional further ingredients is incubated under UHP to achieve demethoxylation of the pectins and gelling of the fruit pulp. The incubation is carried out while subjecting the packages to UHP. The term "UHP" refers to an isostatic pressure of at least about 200 MPa. Preferably the pressure is from about 300 MPa to about 690 MPa, more preferably from about 350 MPa to about 600 MPa, but higher pressures can also be used.

Apparatus for performing UHP treatment of foodstuffs is well known and will not be described further. Suitable equipment is, for example, available from Avure Technology Inc. of Seattle, Wash. Flow International Corp., Kobe Steel, Amahe S A of Spain, and Engineered Pressure Systems (Mass, US and Belgium). Briefly, the apparatus comprises a cylindrical pressure vessel having at least one end that can be opened for loading, and which can then be sealed in pressure-tight fashion. The packaged products to be treated are introduced into the vessel in a suitable holder, and the vessel is filled with a suitable pressurization fluid, typically water or water/glycerol. Further pressurization fluid is pumped in by means of suitable pressure intensifiers to achieve the desired isostatic pressure inside the vessel The duration of the UHP treatment is typically from about 1 minute to about 30 minutes, preferably from about 2 minutes to about 15 minutes, for example from about 4 minutes to about 10 minutes.

The application of UHP to the products causes an instantaneous adiabatic temperature rise in the material under pressure. The magnitude of this temperature rise depends on the pressure, but is typically about 10° C. to 15° C. for a pressure of 400-500 MPa. The resulting peak temperature of the product is referred to as the peak pressurization temperature. The temperature of the material may subsequently fall during the pressurization treatment due to heat loss through the walls of the pressure vessel. In some embodiments, the pressure vessel is heated, for example by an electrical heating element, to maintain the walls of the pressure vessel at or near the peak pressurization temperature, thereby maintaining the product at or near the peak pressurization temperature for the duration of the UHP treatment step. It follows that the temperature of the UHP treatment may be defined by reference to any of the following parameters: (a) the starting temperature of the product immediately before pressurization, (b) the peak temperature reached by the product during pressurization, and/or (c) the temperature at which the thermostat of the pressure vessel is set. Suitably, the starting temperature is about ambient, for example from about 5° C. to about 40° C., preferably from about 10° C. to about 30° C. Suitably, the peak temperature is less than about 70° C., for example from about 20° C. to about 70° C., preferably from about 25° C. to about 50° C. Suitably, the set temperature of the pressure vessel thermostat is from about 20° C. (i.e. no heating) to about 60° C., preferably from about 20° C. to about 50° C., more preferably from about 20° C. to about 40° C. The use of low temperatures gives a stronger gel and furthermore helps to maintain fresh flavor and aroma of the products.

Typical UHP conditions are: vessel temperature 30° C., pressure 400 MPa (which leads to a maximum processing temperature of about 40° C., due to the adiabatic heating), and duration 5 minutes.

The use of UHP provides at least two advantages. Firstly, the adiabatic heating of the sample caused by the application of such high pressure enables the desired heat incubation temperature of about 40° C. to be achieved throughout the package instantaneously without preheating of the package from ambient temperature. This instantaneous heating (optionally assisted by some preheating of the product and/or external heating of the pressure vessel) reduces the total processing time. Secondly, it has been found that when the incubation is carried out under UHP, the resulting products have a distinctive and unique structure. The gel is more homogeneous and coherent than the gels obtained by simple thermal incubation. The gel strength as determined in a texture analyzer by the method described below is substantially higher for the UHP processed samples. This may be due to changes in the hydration and/or the tertiary structure of the pectins under the UHP conditions. It may further be due to collapse of the cell wall structure of the fruit under UHP conditions.

The incubation step results in the packaged fruit product having a coherent, substantially dimensionally stable structure.

The packaged product is also stabilized by the UHP to render it shelf-stable. The term "shelf stable" refers to a product that can be stored at typical chill cabinet temperatures of about 7° C. for a period of at least 1 month, preferably at least 3 months, more preferably at least 6 months and most preferably 1 year, without unacceptable deterioration of organoleptic properties or appearance, or without developing microbiological activity outside regulatory limits. By "ambient stable" is meant a product that can likewise be stored at typical ambient temperatures, such as 20-25° C. at 60% relative humidity, with similar stability.

Preferably, the measured amounts of pathogenic microorganisms in the stabilized product both before and after storage are in the following ranges:

| | |
|---|---|
| *Salmonella*/100 g | absent |
| *E. coli*/g | absent |
| *Enterobacteriaceae*/g | <1 |
| Faecal Strep./g | <10 |
| Yeasts/g | <10 |
| Moulds/g | <10 |
| *B. cereus*/g | <100 |
| *S. Aureus*/g | <20 |
| TVC/g | <100 |
| *Listeria*/25 g | absent |

The UHP treatment is also effective to inactivate spoilage enzymes such as peroxidase and polygalacturonase. The PME is more resistant to heat and pressure, but it has been found, surprisingly, that it is not necessary to inactivate the PME in order to achieve a fully ambient stable product. Accordingly, the processes according to the present invention preferably do not comprise additional stabilizing steps after the UHP treatment.

In order to produce stabilized products at the processing temperatures hereinbefore described it is desirable to apply UHP at pressures of at least about 350 MPa, preferably at least about 400 MPa, for example at least about 500 MPa. Appropriate conditions can be identified by means of suitable challenge tests, in which samples are inoculated with high levels (>log 6) of specific microorganisms and survival of these microorganisms after the UHP processing is monitored. The survival is related to the type of microorganisms, the UHP pressure, temperature and time.

BRIEF DESCRIPTION OF THE DRAWINGS

Specific embodiments of the present invention will now be described further, by way of example, with reference to the accompanying drawings, in which.

DETAILED DESCRIPTION OF THE INVENTION

Figure 1:
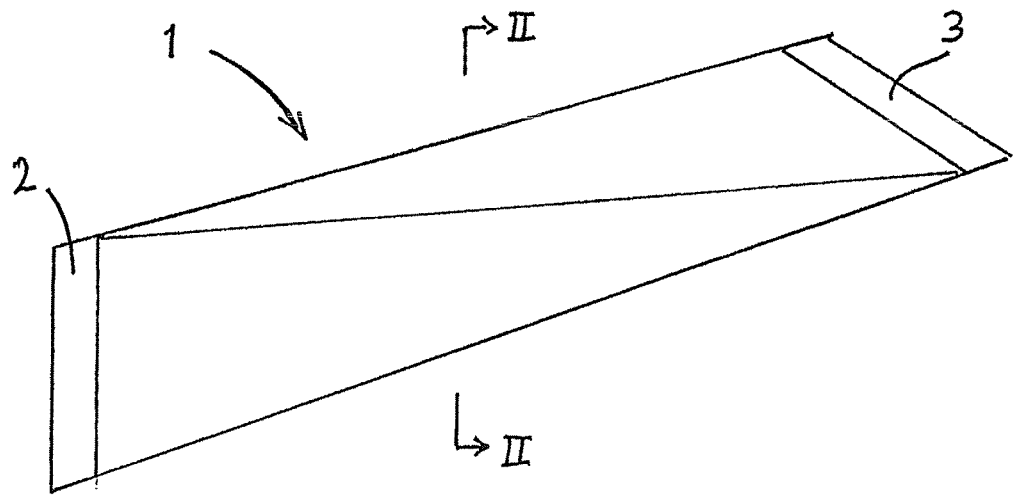
FIG. 1 shows a perspective view of a packaged fruit product according to the present invention.

Referring to FIG. 1, the product 1 is a stick pouch formed from transparent, substantially oxygen-impermeable sheet material. The pouch is formed from a tube of the sheet material that is transversely heat sealed at ends 2,3. The heat seals are oriented at about 90° to one another in order to give the pouch a more attractive appearance. The pouch is substantially completely filled with the gelled fruit product. The pouch is manufactured, filled and sealed using conventional form-fill-seal technology.

Figure 2:
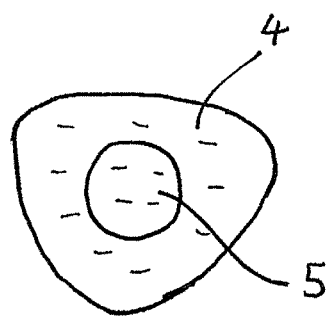
FIG. 2 shows a transverse cross section through the product of FIG. 1 along II-II.

Referring to FIG. 2, the gelled fruit inside the pouch comprises an outer layer 4 of a first fruit composition (e.g. mango) and an inner core 5 of a second fruit composition (e.g. mango with pineapple). The outer layer and core are formed by coextrusion. The inner core comprises a red food coloring to give the product a distinct appearance.

EXAMPLE 1

A packaged fresh mango bar was prepared as follows. Ripe mango (Tommy Atkins variety, Guatemala) was peeled, stoned and chopped to coarse puree. Approximately 0.25% ascorbic acid was added as an antioxidant to protect the product against oxidation. The pH after the addition of ascorbic acid was 3.5.

PME (1800 PE units per kg fruit) was added. The PME was Rapidase® FP Super, a liquid purified PME from a non-GMO strain of *Aspergillus niger*. Minimum activity was 900 PEU/g. It is Kosher and Halal approved, preservative free and suitable for organic production.

The pulp was then filled directly into a stick (pillow) pouch of dimensions approximately length 10 cm, width 4 cm. The pouches were formed from an oxygen barrier film (with $O_2$ transmission rate <2 $cm^3/m^2$/day).

The stick pouches were then immediately passed to a UHP apparatus at ambient temperature and subjected to 350 MPa for 5 minutes (peak temperature about 35° C.), or to 600 MPa for 5 minutes (peak temperature about 40° C.). In both cases, the UHP treatment resulted in a gelled, coherent, dimensionally stable bar within the stick. The bar had a natural mango color and a pleasant, fruit-like structure. The flavor as determined by a taste panel was only very slightly impaired relative to fresh mango. The packaged UHP-treated products were ambient stable for at least 6 weeks. This confirms that the PG has been substantially inactivated by the UHP treatment.

REFERENCE EXAMPLE 2

A mango fruit bar was prepared by a method similar to that of Example 1 but instead of the UHP incubation and stabilization step, separate thermal incubation and stabilization steps were carried out. The thermal incubation carried out at 40° C. for 30 minutes. This resulted in a gelled fruit bar having a coherent structure and dimensional stability with fresh fruit appearance, aroma and taste. The structural integrity of the bar was slightly less than that of the bar produced by UHP, and the texture of the thermally incubated bar was less homogenous, with a weaker matrix and more solid fruit pieces in the matrix.

The thermally incubated bar is then thermally stabilized by heating at 85° C. for five minutes. This minimal thermal processing results in a stabilized fruit bar having substantially natural color, flavor and aroma.

EXAMPLE 3

The process of Example 1 was repeated with a fresh papaya fruit pulp. Ascorbic acid 1 wt. % was added to give a final pH of the pulp of 3.7. PME was added in an amount of 0.2 wt. %. No calcium was added. UHP treatment was carried out at 400 MPa for 5 minutes (first sample) and 10 minutes (second sample) resulting in stabilized, packaged papaya gel products.

EXAMPLE 4

The process of Example 1 was repeated with a fresh apple fruit pulp. Ascorbic acid 1 wt. % was added. PME was added in an amount of 0.2 wt. %. Calcium lactate was added in an amount of 0.54 wt. % (0.1 wt. % calcium). UHP treatment was carried out at 400 MPa for 10 minutes resulting in stabilized, packaged apple gel product.

EXAMPLE 5

The process of Example 1 was repeated with a fresh peach fruit pulp. Ascorbic acid 0.5 wt. % was added to give a pulp having pH 3.21 PME was added in an amount of 0.2 wt. %. Calcium lactate was added in an amount of 0.54 wt. % (0.1 wt. % calcium). UHP treatment was carried out at 400 MPa for 5 minutes resulting in stabilized, packaged peach gel product.

EXAMPLE 6

The process of Example 1 was repeated with addition of papaya pieces to the mango pulp. Ascorbic acid 0.25 wt. % was added to give a pulp having pH 3.5. PME was added in an amount of 0.2 wt. %. No calcium was added. UHP treatment was carried out at 400 MPa for 5 minutes (first sample) or 10 minutes (second sample) resulting in stabilized, packaged mango gel products containing papaya pieces.

EXAMPLE 7

The process of Example 1 was repeated with a mixed fresh fruit pulp containing 75 wt. % apple and 25 wt. % raspberry. PME was added in an amount of 0.2 wt. %. Calcium lactate was added in an amount of 0.54 wt. % (0.1 wt. % calcium). UHP treatment was carried out at 400 MPa for 5 minutes resulting in stabilized, packaged mixed fresh fruit gel product.

EXAMPLE 8

The process of Example 1 was repeated with a fresh strawberry fruit pulp supplied by SVZ. PME was added in an amount of 0.2 wt. %. Calcium lactate was added in an amount of 0.54 wt. % (0.1 wt. % calcium). UHP treatment was carried out at 350 MPa for 5 minutes resulting in stabilized, packaged strawberry gel product.

EXAMPLE 9

The process of example 1 was repeated with a mixture containing 90 wt. % fresh mango and 10 wt. % mango concentrate (42 Brix). PME was added in an amount of 0.2 wt. %. No calcium was added. UHP treatment was carried out at 400 MPa for 5 minutes resulting in stabilized, packaged mango bar.

EXAMPLE 10

A mango pulp containing PME was prepared as described in Example 1. A pineapple pulp containing PME was separately prepared in similar fashion. The mango pulp and pineapple pulp were filled into a pouch stick using concentric filling tubes, whereby the pouch contained a core of pineapple pulp enclosed by a shell of mango pulp of thickness approximately 5 mm. The pouch was then UHP treated as described in Example 1. The resulting stabilized fruit bar comprised a gelled shell of mango enclosing a core of pineapple pulp having lower gel strength.

EXAMPLE 11 AND REFERENCE EXAMPLE 12

The relative gel strengths of products made by UHP incubation and thermal incubation were determined as follows. Ripe mango (Tommy Atkins, Israel) was peeled, stoned and chopped to coarse puree. 0.5 wt. % vitamin C was added. The pH after the addition was 3.78. The pulp was then filled directly into a petri dish with a diameter of 5 cm and 1 cm thickness. The petri dishes were put in a pouch and processed with either UHP (Example 11) or a thermal (Reference Example 12) treatment. For the UHP treatment the apparatus was initially at ambient temperature and subjected to 400 MPa for 5 minutes. The thermal treatment was carried out in a water bath at 40° C. for 30 minutes.

The texture of the products was measured with a Stable Micro Systems texture analyzer. The settings were as follows:

| | |
|---|---|
| Probe diameter: | 2 cm |
| Pre-test speed: | 1.00 mm/sec |
| Test speed: | 2.00 mm/sec |
| Trigger force | 0.020 N |
| Compression distance: | 5 mm |

Six measurements were carried out on each sample. The mean measured forces required to break the gels in Newtons were as follows:

UHP gel (Example 11) 15.01 N (std. dev. 2.68)

Thermal gel (Reference Example 12) 9.52 N (std. dev. 0.38)

These measurements confirmed the observable behavior of the gels, namely that the UHP processed gels were firmer than the gels produced by thermal incubation.

EXAMPLE 13

A mango pulp containing PME was prepared as described in Example 9 and processes at 500 MPa for 5 minutes to produce a gelled mango snack. The soluble and insoluble fiber content of the snack was determined by AOAC Method 991.43. The soluble fiber content was 0.7 wt. % and the insoluble fiber content was also 0.7 wt. %

EXAMPLE 14

A strawberry pulp was prepared from 90 wt. % fresh strawberries and 10 wt. % strawberry concentrate (45 Brix) with 0.2 wt. % PME and 0.4 wt. % calcium lactate, with addition of ascorbic acid to reach a pH of 3.55. The pulp was processed at 400 MPa for 5 minutes at a pressure vessel set temperature of 60° C. to produce a gelled strawberry snack. The soluble and insoluble fiber content of the snack was determined by AOAC Method 991.43. The soluble fiber content was 0.3 wt. % and the insoluble fiber content was 1.4 wt. %

EXAMPLE 15

A 50:50 mixture of fresh cherry tomatoes and pureed fresh mango was mixed and packaged in a stick pouch. No other components were added. The pouch was processed at 600 MPa for 10 minutes at ambient temperature to produce a gelled snack.

EXAMPLES 16-24

The effect of different UHP treatment conditions on texture, flavor and storage properties of mango fruit snacks according to the invention was studied as follows.

Samples were prepared from fresh mango pulp (98.8 wt. %), ascorbic acid (1 wt. %) and fungal PME (0.2 wt. %) and filled into Petri dishes as described in Example 11. The samples were then loaded into a pressure vessel at ambient temperature and subjected to UHP treatment under different conditions and the texture of the resulting gelled products was evaluated by the method described in Example 11. The conditions and results were as follows (the UHP temperature column refers to the set temperature of the pressure vessel):

| Example | UHP Temp (° C.) | UHP Time (Mins) | UHP Pressure (MPa) | Texture (Newtons) |
|---|---|---|---|---|
| 16 | 20 | 4 | 300 | 7.8 |
| 17 | 50 | 4 | 300 | 8.3 |
| 18 | 20 | 10 | 300 | 16.2 |
| 19 | 50 | 10 | 300 | 10.2 |
| 20 | 20 | 4 | 600 | 13.4 |
| 21 | 50 | 4 | 600 | 11.2 |
| 22 | 20 | 10 | 600 | 16.6 |
| 23 | 50 | 10 | 600 | 14.8 |
| 24 | 35 | 7 | 450 | 11.7 |

It can be seen that increasing the treatment time results in a substantially firmer gel. Increasing the pressure and/or lowering the treatment temperature also results in a firmer gel.

Sensory profiling of the products was performed by a taste panel. Significant differences were observed for the parameters of hardness, cohesiveness, fibers and solvability. The discriminant analysis plot showed that all samples processed at the high pressure of 600 MPa had a hard and more cohesive texture, although the effect of time is less clear in comparison to the effect of pressure. No clear effect of temperature on the sensory properties of the finished products could be established. With regard to taste, it was found that increased pressure resulted in a slight increase in perceived acidity. The higher temperature gave a slight cooked note, which was suppressed at the higher pressure. However, the effects of varying the UHP conditions on taste were slight.

The stability of the products was assessed by storage at ambient and chilled temperatures for up to 31 weeks, with microbiological analysis. The samples processed at 300 MPa were spoiled after 24 days ambient storage. The samples processed at higher pressures were shelf stable for at least 31 weeks.

REFERENCE EXAMPLE 25

A comparison experiment was performed in similar fashion to Examples 16-24, but with replacement of the UHP treatment step by a thermal incubation step at 40° C. for 30 minutes. The resulting gelled fruit product was tested for texture and stability. The maximum force in the texture measurement was only about 5.6 Newtons. The sensory analysis determined that the thermally processed product was less hard, less cohesive and more soluble than the UHP treated products. The thermally processed product was spoiled after 24 days storage at ambient temperature.

The above examples have been described by way of illustration only. Many other embodiments falling within the scope of the accompanying claims will be apparent to the skilled reader.

What is claimed is:

1. A packaged, shelf-stable, gelled natural fruit pulp, comprising:
fresh natural fruit pulp having no added hydrocolloids and an added pectinmethylesterase (PME) enzyme, wherein the action of the pectinmethylesterase (PME) enzyme under ultra-high pressure (UHP) conditions demethoxylates the natural pectins of said fruit pulp to form a shelf-stable dimensionally stable fruit gel snack having a texture measurement between 7.8 and 16.6 Newtons.

2. The packaged natural fruit pulp according to claim 1, wherein the pulp comprises at least about 50% by weight of a fruit selected from the group consisting of mango, strawberry, kiwi, papaya, pineapple, apricot, peach, nectarine, cherries, blueberries, raspberries, apple, pear, chestnut, banana, blackberry, cranberry, passion fruit, grapefruit, mandarin, orange, melon, grapes, or mixtures thereof.

3. The packaged natural fruit pulp according to claim 1, wherein the pulp comprises at least about 70 wt. % water and less than about 5 wt. % of insoluble fiber.

4. The packaged natural fruit pulp according to claim 1, further comprising an added divalent metal ion salt to promote gel formation of the demethoxylated pectin.

5. The packaged natural fruit pulp according to claim 1, wherein the pH of the fruit pulp is less than about 4.5.

6. The packaged natural fruit pulp according to claim 1, wherein the fruit pulp comprises an added antioxidant to promote stability.

7. The packaged natural fruit pulp according to claim 1, wherein the fruit pulp comprises the fruit flesh, added PME, and added divalent metal ion salts.

8. The packaged natural fruit pulp according to claim 7, wherein the product is at least about 98 wt. % natural fruit or vegetable ingredients.

9. The packaged natural fruit pulp according claim 1, wherein the packaging comprises a flexible film pouch.

10. The packaged natural fruit pulp according to claim 1, wherein the natural fruit pulp is ambient stable for at least 6 weeks.

11. The packaged natural fruit pulp according to claim 1, wherein a first stabilized gelled pulp occupies a first region of a package, and a second stabilized fruit pulp occupies a second region of said package, whereby said fruit pulps form a unitary, packaged, stabilized fruit product having distinct first and second regions.

12. The packaged, shelf-stable fruit product according to claim 11, wherein the second fruit pulp forms a core of said product and said gelled fruit pulp forms a shell substantially enclosing said core.

13. The packaged natural fruit pulp according to claim 2, wherein the pulp comprises at least about 75% by weight of a fruit selected from the group consisting of mango, strawberry, kiwi, papaya, pineapple, apricot, peach, nectarine, cherries, blueberries, raspberries, apple, pear, chestnut, banana, blackberry, cranberry, passion fruit, grapefruit, mandarin, orange, melon, grapes, or mixtures thereof.

14. The packaged natural fruit pulp according to claim 13, wherein the pulp comprises at least about 95% by weight of a fruit selected from the group consisting of mango, strawberry, kiwi, papaya, pineapple, apricot, peach, nectarine, cherries, blueberries, raspberries, apple, pear, chestnut, banana, blackberry, cranberry, passion fruit, grapefruit, mandarin, orange, melon, grapes, or mixtures thereof.

15. The packaged natural fruit pulp according to claim 3, wherein the pulp comprises at least about 80 wt. % water and less than about 3 wt. % insoluble fiber.

16. The packaged natural fruit pulp according to claim 15, wherein the pulp comprises less than about 2 wt. % of insoluble fiber.

17. The packaged natural fruit pulp according to claim 5, wherein the pH of the fruit pulp is in the range of from about 3 to about 4.

18. The packaged natural fruit pulp according to claim 17, wherein the pH of the fruit pulp is from about 3 to about 3.5.

19. The packaged natural fruit pulp according to claim 7, further including an acidifier.

20. The packaged natural fruit pulp according to claim 7, further including antioxidants.

21. A packaged natural fruit pulp according to claim 7, wherein the product is 100% natural fruit or vegetable ingredients.

* * * * *